US009207144B2

(12) United States Patent
Kouji et al.

(10) Patent No.: US 9,207,144 B2
(45) Date of Patent: Dec. 8, 2015

(54) PINHOLE INSPECTION APPARATUS FOR CAN BODIES (71) Applicant: TOYO SEIKAN GROUP HOLDINGS, LTD., Tokyo (JP)

(72) Inventors: Yasuhiro Kouji, Yokohama (JP); Yuuma Ishii, Ibaraki (JP); Tomoki Seo, Sendai (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 0 days.

(21) Appl. No.: 14/408,455

(22) PCT Filed: Apr. 30, 2013

(86) PCT No.: PCT/JP2013/062600
§ 371 (c)(1),
(2) Date: Dec. 16, 2014

(87) PCT Pub. No.: WO2013/190920
PCT Pub. Date: Dec. 27, 2013

(65) Prior Publication Data
US 2015/0192493 A1    Jul. 9, 2015

(30) Foreign Application Priority Data
Jun. 21, 2012 (JP) .................................. 2012-139988

(51) Int. Cl.
G01M 3/38 (2006.01)
G01N 21/894 (2006.01)
G01N 21/90 (2006.01)

(52) U.S. Cl.
CPC ............... *G01M 3/38* (2013.01); *G01N 21/894* (2013.01); *G01N 21/909* (2013.01); *G01N 2201/062* (2013.01)

(58) Field of Classification Search
CPC ....... G01M 3/38; G01N 21/894; G01N 21/909; G01N 2201/062
USPC ............................................. 356/237.1–241.6
See application file for complete search history.

(56) References Cited

U.S. PATENT DOCUMENTS 835,836 A * 11/1906 Schulz ..................... F01D 11/02
277/419
3,697,758 A * 10/1972 Binks ..................... G01N 21/894
250/202

(Continued)

FOREIGN PATENT DOCUMENTS

JP    64-79646 A    3/1989
JP    9-210924 A    8/1997

(Continued)

OTHER PUBLICATIONS

International Search Report dated Jul. 9, 2013 issued in corresponding application No. PCT/JP2013/062600.

*Primary Examiner* — Gregory J Toatley
*Assistant Examiner* — Jarreas C Underwood
(74) *Attorney, Agent, or Firm* — Westerman, Hattori, Daniels & Adrian, LLP (57) ABSTRACT Provided is a pinhole inspection apparatus for can bodies capable of effectively preventing entrance of ambient light to a photodetector side through a gap between a movable plate and a rotating turret that may be formed due to a surface condition or the like. The pinhole inspection apparatus of the present invention includes: a rotating turret having a penetrating through hole; a movable plate provided on a stationary frame opposite the rotating turret; a can body holding member supporting a can body; a photodetector detecting light leaking inside the can body; and a light source irradiating the can body with light. The pinhole inspection apparatus is characterized in that a detour path formed by a pair of shield parts spaced apart a predetermined distance and opposite from each other is provided as a shield mechanism in an entire outer peripheral region of the rotating turret.

12 Claims, 7 Drawing Sheets

(56) References Cited

U.S. PATENT DOCUMENTS

| | | | | |
|---|---|---|---|---|
| 4,074,809 A | * | 2/1978 | McMillin | B07C 5/3404 209/588 |
| 5,064,284 A | * | 11/1991 | Johnston, Jr. | G01J 1/4257 356/121 |
| 2004/0119238 A1 | * | 6/2004 | Skumawitz | F16J 15/4472 277/412 |

FOREIGN PATENT DOCUMENTS

| | | |
|---|---|---|
| JP | 2002-365230 A | 12/2002 |
| JP | 2003-75360 A | 3/2003 |
| JP | 2004-317356 A | 11/2004 |
| JP | 2009-25131 A | 2/2009 |
| JP | 4230269 B2 | 2/2009 |
| JP | 4715988 B2 | 7/2011 |
| WO | 02/099402 A1 | 12/2002 |

* cited by examiner

Prior Art

PINHOLE INSPECTION APPARATUS FOR CAN BODIES

TECHNICAL FIELD

The present invention relates to an apparatus for inspecting pinholes formed in a body part or the like of can bodies.

BACKGROUND ART

During a production process of metal can bodies such as seamless can bodies produced by drawing with ironing, for example (hereinafter simply referred to as "can body"), pinholes in the form of holes or cracks may be created in a body part or the like of the can body. Commonly, presence or absence of such pinholes is determined by using a pinhole inspection apparatus in an inspection process of can bodies.

Figure 10:
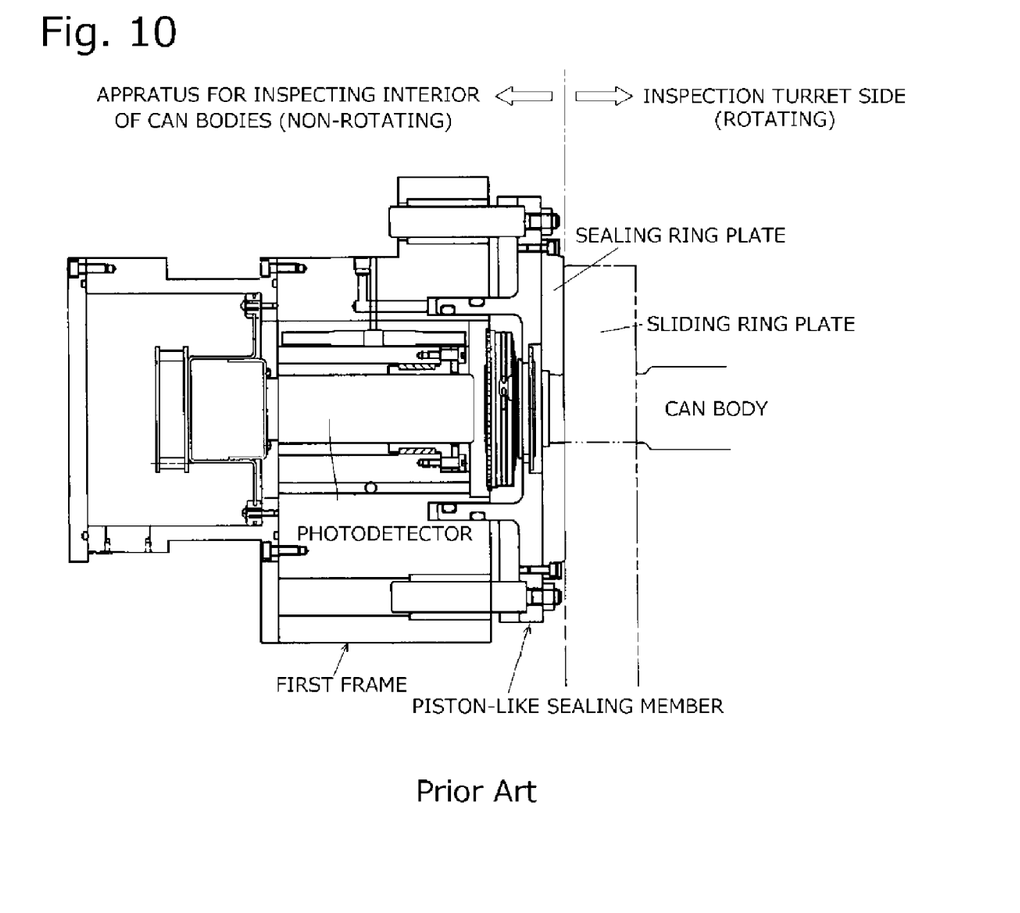
FIG. 10 is a diagram for explaining the configuration of a conventional pinhole inspection apparatus for can bodies.

The pinhole inspection apparatus shown in Patent Document 1 is configured, as shown in FIG. 10, with an inspection turret that holds can bodies to be inspected on the right side, and an apparatus for inspecting the interior of can bodies on the left side. A piston-like sealing member is provided with a sealing ring plate fixedly attached thereto for sealing a sliding contact surface with a sliding ring plate by making sliding contact therewith. The piston-like sealing member is mounted on a distal end face of a first frame on the side facing the sliding ring plate for making the sliding contact. During pinhole inspection, the piston-like sealing member is pressed against the sliding ring plate rotating at a high speed with air pressure, to enhance the sealing effect at the sliding contact surface, and to prevent entrance of ambient light, which is formed of outside light and light from a light source, through the sliding contact surface to a photodetector side.

Since the sealing ring plate is kept in pressure contact with the rapidly rotating sliding ring plate during pinhole inspection as noted above, ambient light normally does not reach the photodetector through the sliding contact surface between the sealing ring plate and the sliding ring plate. However, there was a possibility that ambient light may reach the photodetector through a gap that may be created instantaneously between the sealing ring plate and the sliding ring plate due to various factors such as some form of external force applied thereto, or surface conditions of these plates, and good products may be erroneously determined as defective.

The diameter of pinholes to be inspected by a conventional pinhole inspection apparatus for can bodies is about 20 μm, which is determined by the performance of the photodetector. Pinholes with an even smaller diameter may not pass an enough amount of light into the can body to be detectable. A possible approach would be to secure a sufficient amount of light for enabling detection by the photodetector by using a light source with higher brightness than conventional light sources. However, the conventional apparatus configuration does not have sufficient countermeasures against ambient light, and the increase in the light amount could lead to an increased erroneous detection rate.

Patent Document 2 describes shielding light from a light source with a peripheral portion and an inner edge portion made of aluminum coated with black silicone resin. Patent Document 3 describes a light shield part (cover) that can block light from a light source and prevent light from penetrating between a movable plate and a rotating disc. Neither of these configurations has not fully resolved the problems described above, as ambient light may still pass around the peripheral portion and inner edge portion, or the light shield part (cover), and reach the photodetector side from between the movable plate and rotating disc.

PRIOR ART LITERATURE

Patent Documents

Patent Document 1: Japanese Patent No. 4715988
Patent Document 2: Japanese Patent Application Laid-open No. 2002-365230
Patent Document 3: Japanese Patent No. 4230269

SUMMARY OF THE INVENTION

Problems to be Solved by the Invention

Based on the problems described above, a first object of the present invention is to provide a pinhole inspection apparatus for can bodies capable of effectively preventing entrance of ambient light to a photodetector side through a gap between a movable plate and a rotating turret that may be formed due to a surface condition or the like. A second object is to provide a pinhole inspection apparatus for can bodies with improved inspection precision, which is capable of detecting even smaller pinholes owing to the use of a light source with higher brightness that is enabled by achieving the first object.

Means for Solving the Problems

A pinhole inspection apparatus for can bodies of the present invention includes a rotating turret having a penetrating through hole, a movable plate provided on a stationary frame opposite the rotating turret, a can body holding member on which a body part of a can body is placed, a photodetector detecting light leaking inside the can body, and a light source irradiating the can body with light, characterized in that a detour path formed by a pair of shield parts spaced apart a predetermined distance and opposite from each other is provided as a shield mechanism in an entire outer peripheral region of the rotating turret.

The pinhole inspection apparatus for can bodies of the present invention may adopt the following forms:

1. The pair of shield parts include a first shield part and a second shield part, the first shield part being fixedly attached to the rotating turret, and the second shield part being fixedly attached to a position substantially opposite a side face part of the rotating turret.

2. The pair of shield parts include a first shield part and a second shield part, and shield members provided to the respective shield parts protrude alternately toward tubular parts of the respective shield parts opposite each other.

3. The shield members are shield plates protruding orthogonally to the tubular parts of respective shield parts opposite each other.

4. The shield member faces another shield member with a distance of 5 mm or less.

5. The shield member overlaps another shield member opposite thereto over a length of 9 mm or more.

6. A plurality of annular grooves having a rectangular cross section and concentric to a penetrating hole of the movable plate are formed in a surface of the movable part as a shield mechanism.

7. The apparatus includes a light source that irradiates an outer circumferential surface of the can body with light, the light source being a white LED light source.

8. The can body holding member is secured to a support shaft of a chuck via a rod.

Effects of the Invention

The pinhole inspection apparatus for can bodies of the present invention includes a complex structured detour path provided as a shield mechanism, so that it is possible to attenuate or shield ambient light as the light propagates through the detour path, and to effectively prevent entrance of ambient light to the photodetector side through a gap between the movable plate and the rotating turret.

The pair of shield parts include a first shield part and a second shield part, the first shield part being fixedly attached to the rotating turret, and the second shield part being fixedly attached to an end of a case that covers a stationary frame, whereby the pair of shield parts can have a stable predetermined distance, which enables stable attenuation or shielding of ambient light as the light propagates through the detour path, and effectively prevents contact between the shield parts.

As the shield members provided to the first shield part and second shield part protrude alternately toward tubular parts of the respective shield parts opposite each other, the propagation path of ambient light is made long, so that ambient light can be effectively attenuated or shielded.

Since the shield members are formed as shield plates that protrude orthogonally toward the tubular parts of the respective shield parts opposite each other, the pair of shield parts that are arranged opposite each other can be readily attached, and also, contact between the shield parts can be prevented. With the shield members formed as thin shield plates, the number of shield members formable on the respective shield parts can be increased, to make the detour path even more complex within a limited range, whereby the effect of attenuating or shielding ambient light can be increased even more.

Since the shield member faces another shield member with a distance of 5 mm or less, the propagation path in the detour path can be made narrow, while contact between the first shield part and second shield part that may occur due to rotation of the rotating turret is prevented, so that ambient light can be effectively attenuated or shielded.

Since the shield member overlaps another shield member opposite thereto over a length of 9 mm or more, the effect of attenuating or shielding ambient light can be increased further.

The movable part may be formed with a shield mechanism formed by annular grooves with a rectangular cross section, so that ambient light that has penetrated through a gap between the rotating turret that is rotating at a high speed and the movable plate is attenuated or absorbed every time the light reaches the space inside the annular groove, whereby the amount of light that reaches the penetrating hole formed in the movable plate can be effectively reduced, and the ambient light is effectively prevented from reaching the photodetector side. Therefore, in combination with the shield mechanism provided to the entire outer peripheral region of the rotating turret described above, the effect of attenuating or shielding ambient light can be increased further.

Since the pinhole inspection apparatus for can bodies of the present invention can employ a high brightness light source, it can use a white LED light source instead of the conventional fluorescent light as the light source for irradiating an outer circumferential surface of the can body with light, so that the apparatus can detect pinholes with an even smaller diameter (of about several μm), while effectively preventing entrance of ambient light to the photodetector side.

With the use of a can body holding member attached to a rod that is secured to a support shaft of a chuck, the inspection turret (star wheel) is made unnecessary, so that the degree of freedom for installing the light source (in particular, lower light source) for irradiating the can body with light is increased, and therefore it is possible to provide more light sources to increase the light amount. Also, defects such as scars or dents in the body part of the can body, which may result from sliding with the end face of the pocket of the inspection turret as the can body moves axially relative to the rotating turret, can be prevented.

EXPLANATION OF REFERENCE NUMERALS

1: Can body
2: Feed-in turret
3: Inspection turret
3*a*: Pocket
3*r*: Rod
4: Feed-out turret
5: Rotating turret
6: Chuck
9: Support shaft
10: Light source
10*a*, 10*b*: Upper and lower light sources
11: Stationary frame
12: Casing
13: Photodetector (photomultiplier tube)
20: Movable plate
21: Penetrating hole
22: Piston member
25: Ring plate
26: Sliding member
27*a* to 27*g*: Annular groove
30: First shield part
31: Tubular part
32*a*, 32*b*: Shield member
40: Second shield part
41: Tubular part
42*a*, 42*b*: Shield member

MODES FOR CARRYING OUT THE INVENTION

One embodiment of a pinhole inspection apparatus for can bodies of the present invention will be described.

Figure 1:
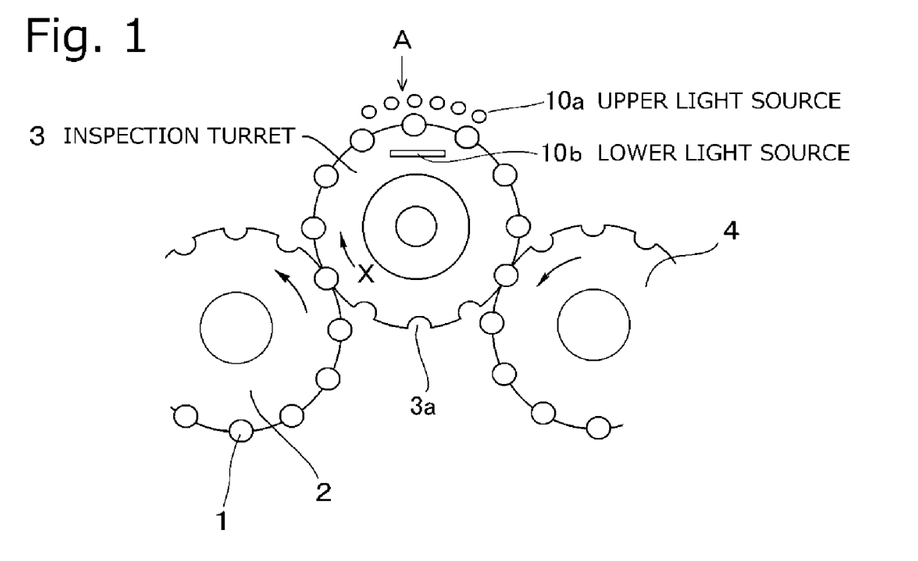
FIG. 1 is a schematic diagram for explaining one form of inspecting can bodies with a pinhole inspection apparatus for can bodies of the present invention.

FIG. 1 is a schematic diagram for explaining one form of inspecting can bodies with the pinhole inspection apparatus for can bodies of the present invention. The drawing shows the process steps of feeding a can body 1, with a feed-in turret 2, to a pocket 3a of an inspection turret 3, which rotates continuously in direction X and transfers the can body to an inspection station A where light sources 10a and 10b to be described later are located and the can body is tested, after which the can body is transferred to a next process by a feed-out turret 4.

Figure 2:
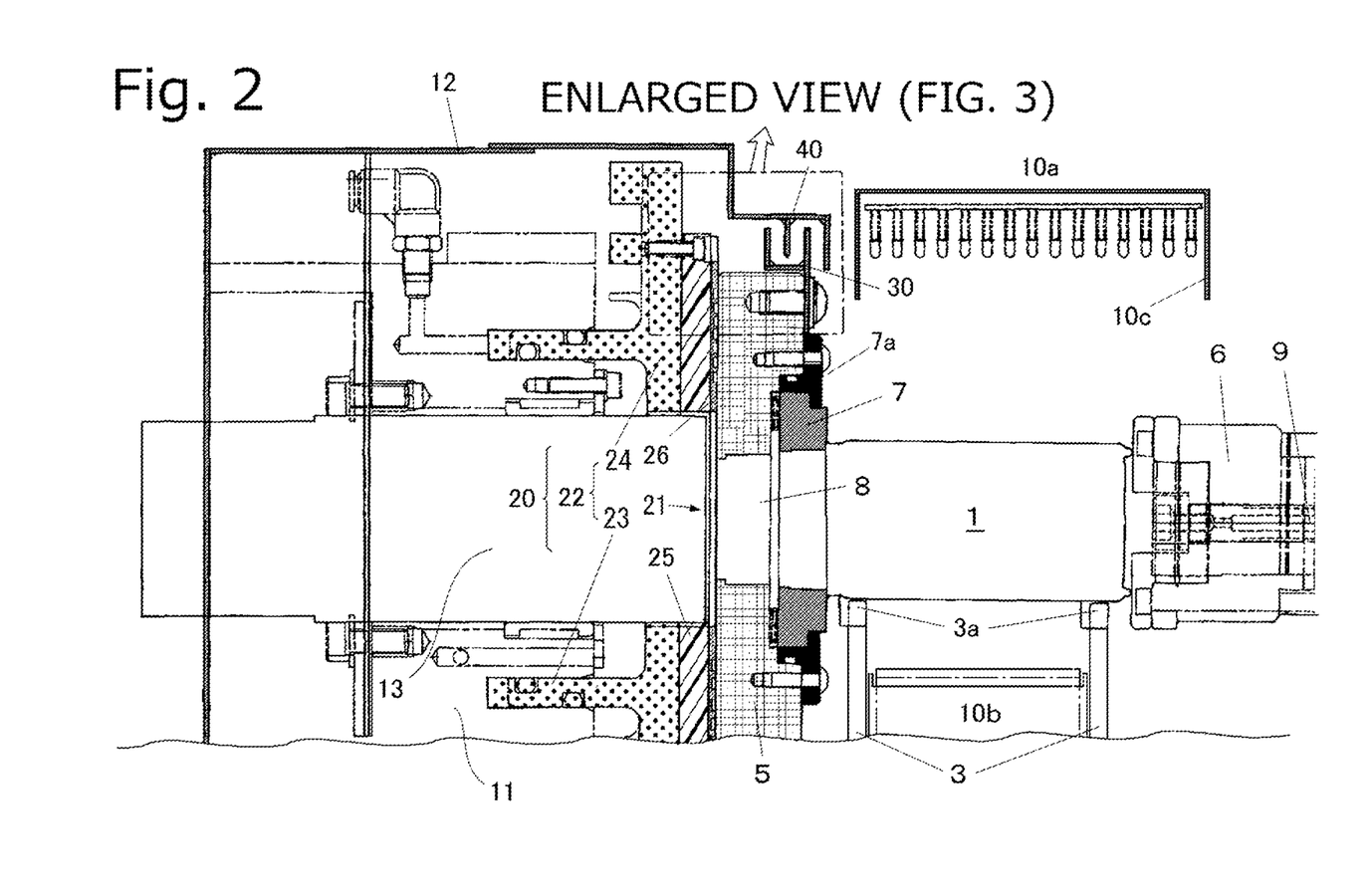
FIG. 2 is a diagram illustrating an inspection region of the pinhole inspection apparatus for can bodies of the present invention.

FIG. 2 is a diagram illustrating an inspection region of the pinhole inspection apparatus for can bodies of the present invention.

The pinhole inspection apparatus for can bodies of the present invention includes the inspection turret 3, a rotating turret 5, a chuck 6, and a light source 10 (10a, 10b). The inspection turret 3 is a can body holding member commonly referred to as star wheel on which can bodies 1 are placed, and formed with a plurality of pockets 3a, which are recesses where the body part of the can body 1 can be placed, along the outer peripheral edge thereof. The rotating turret 5 has a plurality of through holes 8 penetrating through both sides thereof. An open end receiving part 7 of a sponge material, to which the open end of the open-ended can body 1 is pressed, is attached to one peripheral edge of the through hole 8 via an attachment ring 7a. The chuck 6 is a member that holds the bottom of the can body 1 by vacuum suction, and fixedly attached on a support shaft 9 and arranged opposite the rotating turret 5. The chuck 6 and the support shaft 9 are movable along an axial direction relative to the rotating turret 5 to bring the open end of the can body 1 into tight contact with the open end receiving part 7 of the rotating turret 5 by means of a cam and a cam follower (not shown).

A stationary frame 11 is covered by a casing 12. Inside the frame is provided a highly sensitive photodetector 13 such as a photomultiplier tube opposite the rotating turret 5 and coaxially to the through hole 8 and a penetrating hole 21 of a movable plate 20 to be described later to detect light leaking inside the can body 1.

In this configuration, light sources 10a and 10b are arranged for irradiating a body part of the can body 1 with light from above and below when the can body 1 that is held and supported by the pocket 3a and the chuck 6 has moved to a position opposite the photodetector 13 set in the stationary frame 11 (inspection station A). A cover 10c is attached to the light source 10a for preventing light from the light source from leaking to the outside of the apparatus.

The light source for this type of pinhole inspection should preferably emit white light including the whole range of wavelengths from ultraviolet light to infrared light. This embodiment employs a plurality of arrayed white LED lights as a high brightness light source. This allows for detection of smaller pinholes with improved inspection precision, while entrance of ambient light to the photodetector 13 side is effectively prevented by the shield mechanism to be described later.

Parts including a piston member 22 having a penetrating hole in the center, a ring plate 25, and a sliding member 26 are collectively called the movable plate 20, which is arranged opposite the rotating turret 5. The piston member 22 is formed by a tubular leg 23 and a top plate 24, and the ring plate 25 is fastened to the top plate 24 by bolts. The sliding member 26 made of a black, non-gloss, and relatively soft plastic with a low friction coefficient, such as a fluorine resin-based soft plastic, is bonded to the top surface of this ring plate 25 to ensure smooth sliding with the rotating turret 5.

The sliding member 26 should preferably be bonded to the ring plate 25 that is fastened to the top plate 24 of the piston member 22 as in this embodiment, but alternatively may be bonded directly to the top plate 24 of the piston member 22.

The leg 23 of the piston member 22 is fitted in a fitting guide groove formed in the stationary frame 11 so that it can reciprocate to and from the rotating turret 5 by piston action with air pressure. To provide a seal in the sliding parts of the leg 23 and the fitting guide groove, a pair of O-rings are provided in the inner and outer circumferential parts of the leg 23. With such a configuration, the movable plate 20 is pressed to make sliding contact with the rotating turret 5 to seal the sliding contact surface, so that ambient light is prevented from penetrating from the sliding surface to the photodetector 13 side.

During inspection of can bodies 1 successively conveyed by continuous rotation, the can body 1 held in the pocket 3a is rotatably supported by the chuck 6, with its open end being in tight contact with the open end receiving part 7 of the rotating turret 5. The can body is then illuminated by the light sources 10a and 10b in the inspection station A, and when the through hole 8 of the rotating turret 5 comes to be coaxial with the penetrating hole 21 of the movable plate 20 (sensing position), light leaking into the can body 1 is received by the photodetector 13, and presence or absence of a pinhole is determined based on the brightness of light.

In this embodiment, a detour path formed by a pair of shield parts spaced apart a predetermined distance and opposite from each other is provided as a shield mechanism in an entire outer peripheral region of the rotating turret. That is, with a complex structured detour path provided as the shield mechanism, it is possible to attenuate or shield ambient light as the light propagates through the detour path, whereby entrance of ambient light to the photodetector side from between the movable plate and the rotating turret is effectively prevented.

Figure 3:
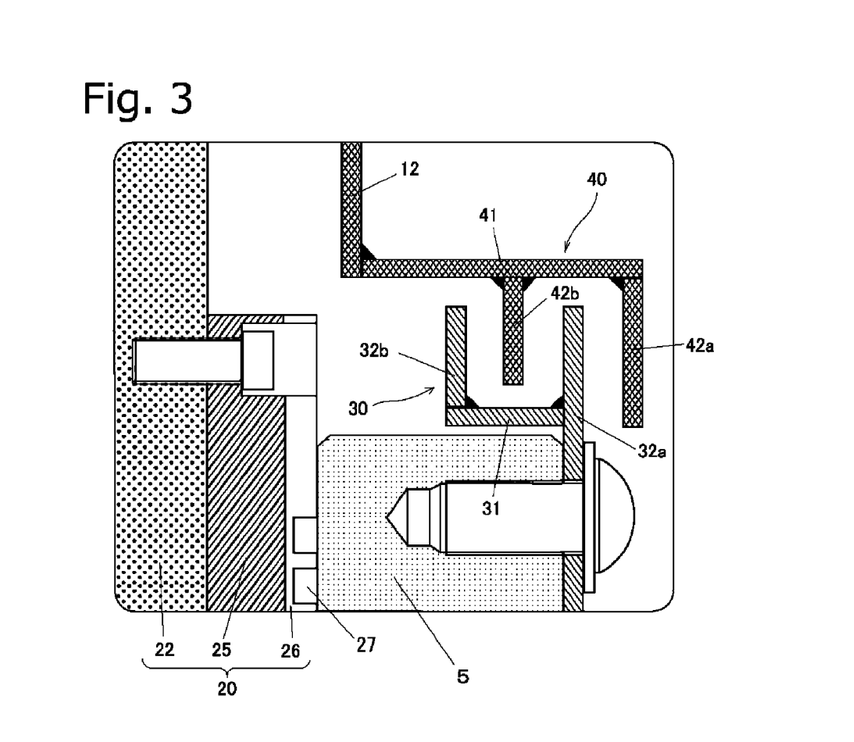
FIG. 3 is an enlarged view of essential parts of a shield mechanism provided to an entire outer peripheral region of the rotating turret in FIG. 2.

As shown in FIG. 2 and FIG. 3, the pair of shield parts are a first shield part 30 attached to the rotating turret 5 by bolts or the like, and a second shield part 40 fixedly attached to a position substantially opposite a side face part of the rotating turret 5, which is, in this embodiment, a distal end of the casing 12 that covers the stationary frame 11. This way, the pair of shield parts can have a stable predetermined distance, which enables stable attenuation or shielding of ambient light as the light propagates through the detour path, and effectively prevents contact between the shield parts.

More specifically, the first shield part 30 includes a tubular part 31 that surrounds an entire outer peripheral region of the rotating turret 5 and extends a predetermined length along a thickness direction of the rotating turret 5, and a plurality of shield members 32a and 32b attached to protrude from the surface of the tubular part 31 toward the second shield part 40. The second shield part 40 includes a tubular part 41 that surrounds an outer peripheral region of the side face part of the rotating turret 5 and extends a predetermined length along the thickness direction of the rotating turret 5, and a plurality of shield members 42a and 42b attached to protrude from the surface of this tubular part 41 toward the first shield part 30.

The first shield part 30 and second shield part 40, i.e., the tubular parts 31 and 41, and respective shield members 32a and 32b, and 42a and 42b (hereinafter referred to as shield members 32 and 42), are spaced a predetermined distance apart so as not to contact each other while facing each other, so that they do not interfere rotation of the rotating turret 5.

The shield mechanism is made of a metal material such as aluminum, steel or the like, with a non-gloss, black surface treatment to absorb, and reduce reflectivity of, ambient light.

The effect of the shield mechanism formed by the first shield part and second shield part provided to the entire outer peripheral region of the rotating turret of the present invention will be discussed with reference to FIG. 4.

In this embodiment, shield members 32 are attached to two locations (32a, 32b) of the first shield part 30, and shield members 42 are attached to two locations (42a, 42b) of the second shield part 40 such as to alternately protrude to the respective tubular parts of the opposite shield parts, with a distance 11 between one shield member and another shield member opposite thereto. With such a configuration, the propagation path of ambient light can be formed long, so that ambient light can be effectively attenuated or shielded.

Since the shield members 32 and 42 are formed as shield plates that protrude orthogonally toward the respective tubular parts 31 and 41 of the opposing shield parts 30 and 40, the pair of shield parts 30 and 40 that are arranged opposite each other can be readily attached, and also, contact between the shield parts 30 and 40 can be prevented. With the shield members 32 and 42 formed as thin shield plates, the number of shield members 32 and 42 formable on the respective shield parts 30 and 40 can be increased, to make the detour path even more complex within a limited range, whereby the effect of attenuating or shielding ambient light can be increased even more.

The shorter the distance 11 is, the higher the light shielding effect, and the more the shield members 32 and 42 are provided, the higher the light shielding effect. The shield members 32 and 42 have a length of ½ or more of a distance 12 between the tubular parts 31 and 41, so that shield members 32a and 32b overlap the opposing shield members 42a and 42b. The longer the overlap length 13 is, the higher the light shielding effect.

In this embodiment, with the distance 11 being 5 mm or less, and with the overlap length 13 being 9 mm or more when the distance 11 is 5 mm, the propagation path in the detour path can be made narrow, while contact between the first shield part 30 and second shield part 40 that may occur due to rotation of the rotating turret 5 is prevented, so that ambient light can be effectively attenuated or shielded. With the distance 11 being more than 5 mm, the propagation path in the detour path will be wide, and if the overlap length 13 is less than 9 mm, the propagation path in the detour path will be short, and in both cases it may be difficult to effectively attenuate or shield ambient light.

The shield members 32 and 42 may have a length, distance, and angle suitably set within a range so that they will not inhibit rotation of the rotating turret 5.

Ambient light to be shielded is the direct light projected from the light sources 10a and 10b, and reflected light from the can body 1 or various parts of the pinhole inspection apparatus. In FIG. 4, the ambient light entering the shield mechanism formed by the first shield part 30 and second shield part 40 is illustrated as light beams A, B, and C from below. Using these light beams from three directions as samples, how a light beam in a specular direction propagates, which is reflected most strongly according to the Gaussian distribution, will be discussed. In FIG. 2 and FIG. 4, from the light sources 10a and 10b side, the region between the shield member 42a and the shield member 32a will be referred to as first region, the region between the shield member 32a and the shield member 42b will be referred to as second region, the region between the shield member 42b and the shield member 32b will be referred to as third region, and the region from the shield member 32b further on will be referred to as fourth region.

Light beam A is incident at a small angle to the surface of the shield member 32a, reflected several times between an inner surface of the tubular part 41 of the second shield part 40 and the distal end face of the shield member 32a, after which it is reflected several times inside the second region. Namely, light beam A cannot go beyond the second region. Provided that the reflectivity is 1/n, the light amount after it is reflected ten times, for example, is $(1/n)^{10}$ of the incident light amount, which is sufficiently low.

Light beam B is incident at a slightly larger angle to the surface of the shield member 32a, and similarly reflected several times between the inner surface of the tubular part 41 of the second shield part 40 and the distal end face of the shield member 32a, after which it is reflected several times inside the second region, bouncing off the shield member 42b. Namely, light beam B cannot go beyond the second region, either, and the light amount after it is reflected ten times, for example, is $(1/n)^{10}$ of the incident light amount, which is sufficiently low.

Light beam C is incident at a large angle to the surface of the shield member 32a, reflected several times inside the first region, after which it enters the second region via the inner surface of the tubular part 41 and is reflected several times inside the second region. It then enters the third region via an outer surface of the tubular part 31 and is reflected several times inside the third region, and reaches the fourth region, again via the inner surface of the tubular part 41. Namely, light beam C reaches the fourth region, which should actually be prevented, but since it is reflected many times inside the shield mechanism (fifteen times in this embodiment), the light amount is $(1/n)^{15}$ of the incident light amount, which is even lower than that of light beams A and B, whose light amount is sufficiently low. Therefore, even if there is created a gap instantaneously between the movable plate 20 and the rotating turret 5, an erroneous operation of the photodetector 13 by light beam C (ambient light) can be effectively prevented, as compared to the conventional configuration.

With the shield mechanism provided to the entire outer peripheral region of the rotating turret of the present invention, as can be seen from the analysis of the reflection behaviors of the three sample light beams, ambient light that has entered the first region cannot easily reach the fourth region because of the reflection phenomenon. Also, as mentioned above, at least the surfaces of the first shield part 30 and second shield part 40 (surfaces forming the detour path) have a black, non-gloss surface treatment, it is reasonable to understand that the reflected light is scattered, i.e., the reflected light is actually scattered in all directions on the surfaces of the first shield part 30 and second shield part 40 and this scattering is repeated. Therefore, the amount of propagated light will be reduced successively from the first region to the second region, and from the second region onwards.

The shield mechanism provided to the entire outer peripheral region of the rotating turret of the present invention may be changed variously.

Figure 4:
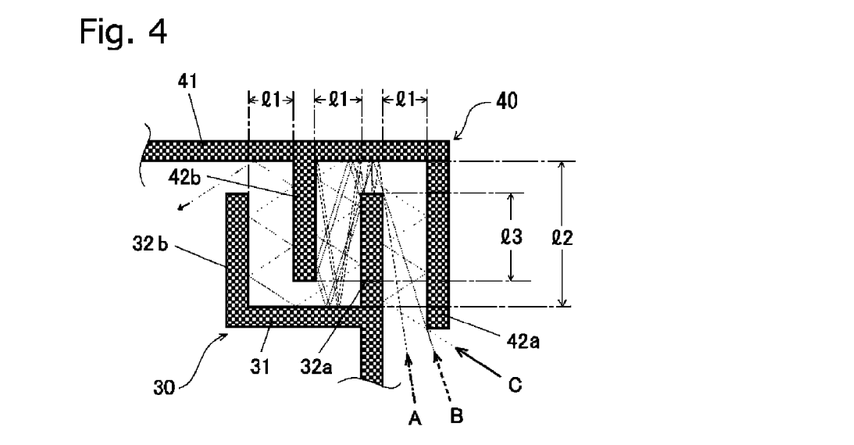
FIG. 4 is a diagram for explaining the shielding function of the shield mechanism provided to the entire outer peripheral region of the rotating turret of the present invention.

For example, as shown in FIG. 4, the length of the shield member 42a may be extended to near the bolt for attaching the first shield part 30, to make the propagation path of ambient light longer, so that ambient light can be effectively attenuated or shielded.

Figure 5:
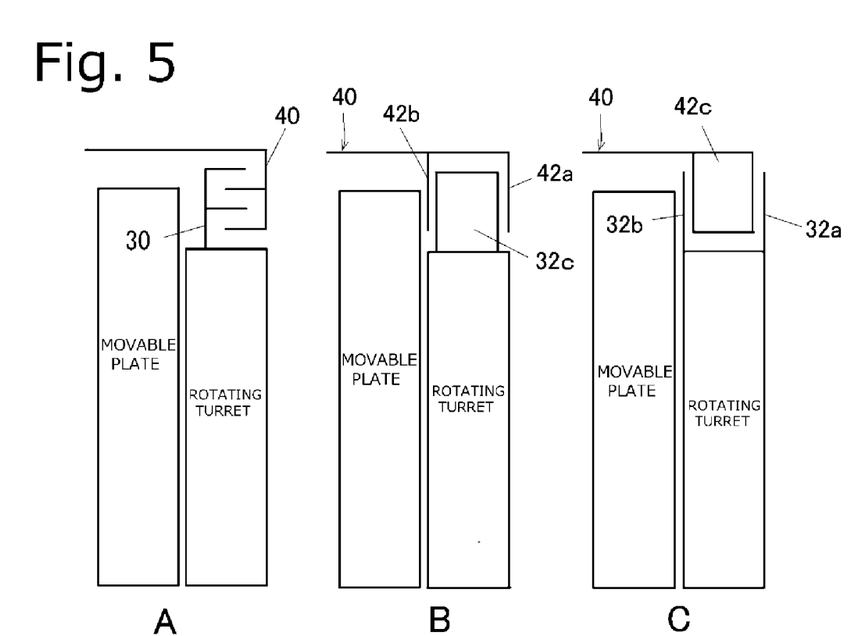
FIG. 5 is a diagram illustrating modified examples of the shield mechanism provided to the entire outer peripheral region of the rotating turret according to the present invention.

As shown in FIG. 5(A), the shield parts 30 and 40 may be attached along the axial direction of the rotating turret 5, with their respective shield members spaced apart the distance l1.

As shown in FIG. 5(B), the respective tubular parts and shield members of the first shield part 30 and second shield part 40 can be formed by materials with a suitable thickness within a certain range as long as they do not inhibit rotation of the rotating turret 5. For example, the first shield part 30 may be an annular block 32c, and arranged between the shield members 42a and 42b of the second shield part 40 with the distance 11 therebetween. Conversely, as shown in FIG. 5(C), the second shield part 40 may be configured as an annular block 42c.

Further, the respective tubular parts and shield members of the first shield part 30 and second shield part 40 may have irregularities on their surfaces (such as recessed grooves), whereby ambient light that has entered the shield mechanism can be scattered even more, and an even higher light shielding effect can be achieved.

As described above, the shield mechanism of the present invention can employ a variety of forms with a high light shielding effect in accordance with the apparatus configuration and desired light shielding effect.

Next, test data that shows the shielding effects, such as attenuation or shielding of ambient light, of the shield mechanism provided to the entire outer peripheral region of the rotating turret of the present invention described above will be shown.

1. Test 1

Various constituent elements of the shield mechanism were made from a 2 mm thick aluminum plate with a black, non-gloss surface treatment, with dimensions set as follows:

<First Shield Part 30>
  Length of tubular part 31=15 mm
  Length of shield members 32a and 32b=12 mm
<Second Shield Part 40>
  Length of tubular part 41=30 mm
  Length of shield member 42a=17 mm
  Length of shield member 42b=12 mm
<Others>
  Distance 11: 5 mm
  Distance 12: 15 mm
  Overlap length 13: 9 mm One can body 1 is held on a given pocket 3a of the inspection turret 3 of the pinhole inspection apparatus, and the open end of the can body 1 is brought into contact with the open end receiving part 7. The rotating turret 5 is rotated gradually and positioned such that the through hole 8 in the rotating turret 5 is coaxial with the penetrating hole 21 in the movable plate 20, whereupon the rotating turret 5 is stopped to perform pinhole inspection.

To confirm the shielding effect of the shield mechanism, the air cylinder for pressing the movable plate 20 was not operated on purpose so that there was a gap of 0.08 mm between the movable plate 20 and the rotating turret 5. The shielding effect with and without the shield mechanism was ascertained based on the light detection values of the photodetector 13.

The light detection value was 125 my when the shield mechanism was provided, with a maximum instantaneous value being 220 mV, while the light detection value was 4900 my or more when the shield mechanism was not provided (which was the upper measurement limit of the photodetector).

The light detection values mentioned above are voltage values (mV) converted from the detected light amount.

Figure 6:
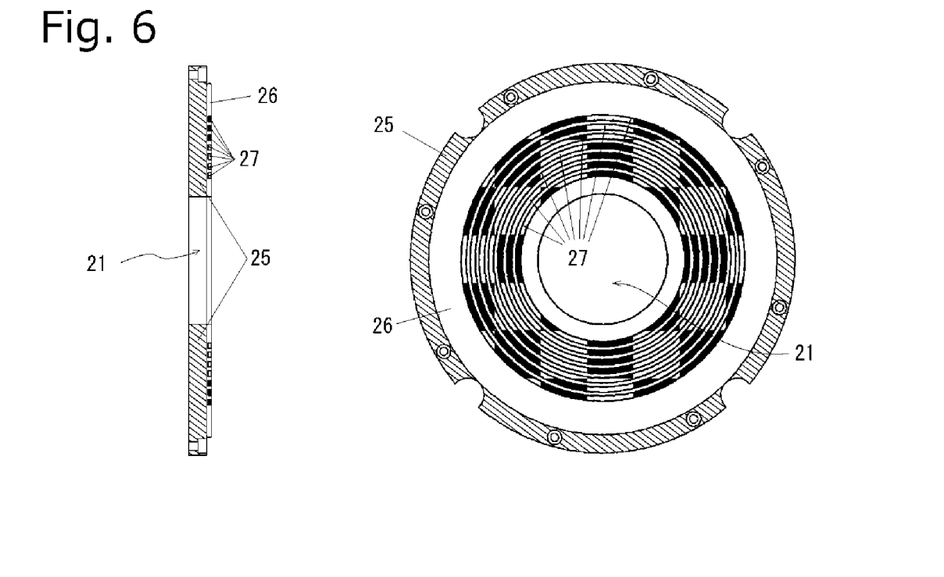
FIG. 6 shows a cross section and a plan view of the shield mechanism formed on the surface of a movable plate of the present invention.
Figure 7:
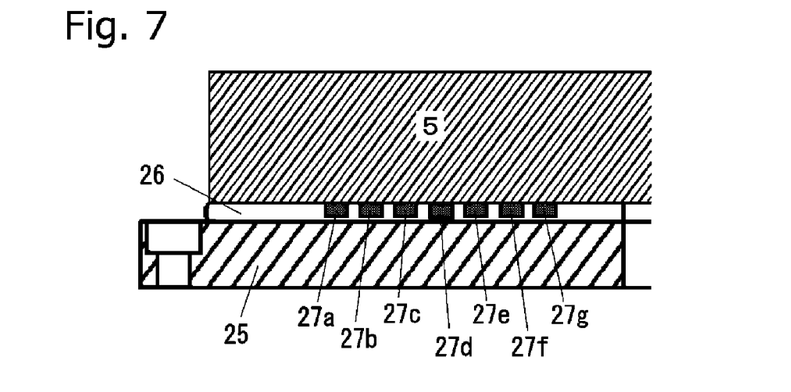
FIG. 7 is a partial enlarged view of the shield mechanism formed on the surface of the movable plate and the rotating turret in sliding contact with each other.

FIG. 6 and FIG. 7 show an example of embodiment in which a plurality of (seven in this example) annular grooves 27 having a rectangular cross section and concentric to the penetrating hole 21 are formed in the surface of the sliding member 26 of the movable plate 20 described above as a shield mechanism. The movable plate 20 configured as described above can effectively reduce the amount of light that reaches the penetrating hole 21 formed in the movable plate 20, and effectively prevent ambient light from reaching the photodetector 13 side, as the ambient light that has penetrated through a gap between the rotating turret 5 that is rotating at a high speed and the movable plate 20 is attenuated or absorbed every time the light reaches the space inside the annular groove 27 having a rectangular cross section of the movable plate 20.

By using such a shield mechanism of the movable plate 20 in combination with the shield mechanism provided to the entire outer peripheral region of the rotating turret described above, the effect of attenuating or shielding ambient light can be increased further.

Figure 8:
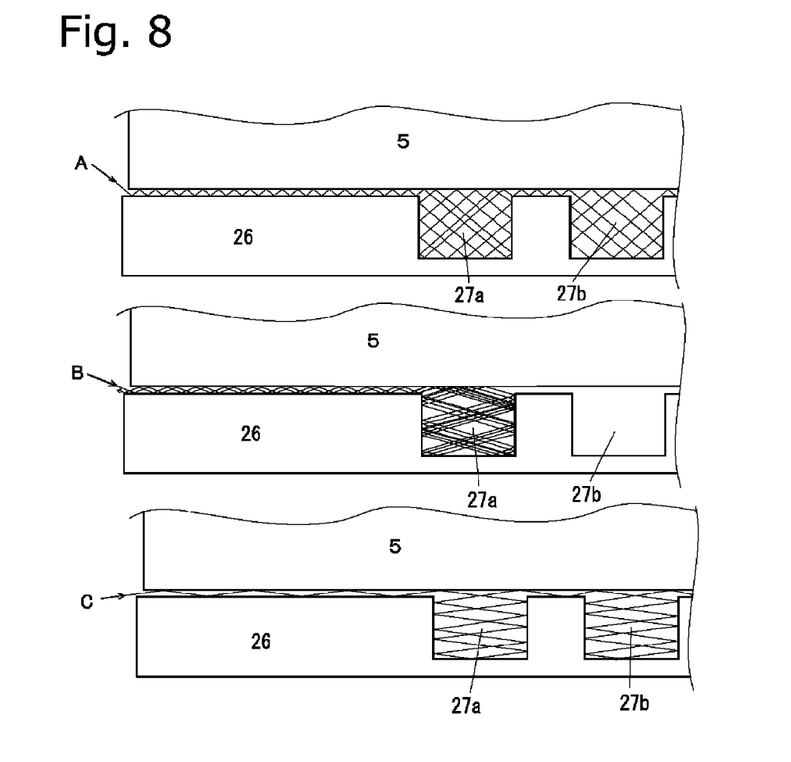
FIG. 8 is a diagram for explaining the shielding function by the shield mechanism formed on the surface of the movable plate of the present invention.

FIG. 8 is a diagram for explaining the shielding function of the shield mechanism of the movable plate 20. Ambient light that penetrates through a gap between the rotating turret 5 and the movable plate 20 at a peripheral portion is the direct light projected from the upper light source 10a and lower light source 10b, and reflected light from the can body 1 or various parts of the pinhole inspection apparatus, and illustrated as light beams A, B, and C from the left side in FIG. 8. Using these light beams from the left side as samples, how a light beam in a specular direction propagates, which is reflected most strongly according to the Gaussian distribution, will be discussed.

Light beams A to C incident on the surface of the sliding member 26 of the movable plate 20 propagate toward the center as they are repeatedly reflected in the gap, and reach the annular groove 27a having a rectangular cross section. When light beams A to C reach the space in the annular groove 27a, they are attenuated or absorbed as they are reflected multiple times by the wall surfaces of the annular groove 27a. When light beams A to C with a reduced light amount then propagate further inward (toward the center) while being repeatedly reflected, and reach the annular groove 27b, they are attenuated or absorbed similarly as they are reflected multiple times. The incident angle of the light beams is progressively smaller in the order of A, B, and C, and the number of times of reflection is also progressively smaller in the order of A, B, and C. Light beam B, after entering the annular groove 27a and being reflected several times, is returned to the entrance of the gap and released outside.

Ambient light that enters at an angle parallel to the surface of the rotating turret 5 and of the sliding member 26 of the movable plate 20 is reflected fewer times and can hardly be attenuated normally. However, since the annular groove 27a forms a relatively wide space as compared to the gap through which the light has been repeatedly reflected, light beams A to C are diffused and attenuated when they reach the space in the annular groove 27a. That is, the light amount of even the ambient light incident at a parallel angle can also be reduced sufficiently by the attenuating effect described above.

As can be seen from the analysis of the reflection behaviors of the three sample light beams, with the shield mechanism formed by a plurality of annular grooves 27 on the surface of the sliding member 26 of the movable plate 20, the light amount of ambient light that has entered the gap can be reduced sufficiently, as the light attenuating effect is superposed every time the light reaches another annular groove 27 on the inner side.

Also, as mentioned above, the surfaces of the rotating turret 5 and the sliding member 26 are black and non-gloss by a surface treatment, so that it is reasonable to understand that the reflected light is scattered, i.e., the reflected light is actually scattered in all directions on the surfaces of the rotating turret 5 and the sliding member 26 and this scattering is repeated. Therefore, the amount of propagated light will be reduced successively from the annular groove 27a to the annular groove 27b, and from the annular groove 27b onwards.

Next, test data that shows the shielding effects, such as attenuation or shielding of ambient light, of the shield mechanism of the movable plate 20 described above will be shown.

2. Test 2

Various parts of the sliding member 26 having a black, non-gloss surface made of a fluorine resin-based soft plastic of the movable plate 20 were set as follows:
Diameter of sliding member 26: ϕ192 mm
Diameter of penetrating hole 21: ϕ71 mm
Diameter of annular groove 27a at the center: ϕ153 mm
Diameter of annular groove 27b at the center: ϕ143 mm
Diameter of annular groove 27c at the center: ϕ133 mm
Diameter of annular groove 27d at the center: ϕ123 mm
Diameter of annular groove 27e at the center: ϕ113 mm
Diameter of annular groove 27f at the center: ϕ103 mm
Diameter of annular groove 27g at the center: ϕ93 mm
Width and depth of annular grooves 27a to 27g: 7.3 mm and 1.5 mm <Measurement Position>

The light amount was measured by the photodetector 13 at positions −12°, −6°, 0°, 6°, and 12°, wherein the angle at which the core axis of the can body 1 matches the axial center of the photodetector 13 is 0°, the positive angles denoting the angles of the rotating turret 5 that has rotated clockwise, and the negative angles denoting the angles of the rotating turret retarding counterclockwise. The angles of −12° and 12° here respectively indicate the starting point and end point where a peripheral edge of the through hole 8 of the rotating turret 5 and a peripheral edge of the penetrating hole 21 of the movable plate 20 overlap. Table 1 shows the data results. Measurements are made in the pinhole inspection apparatus of the present invention when the angle is in the range of from −3° to 3°.

<Measurement Method>

One can body 1 is held on a given pocket 3a of the inspection turret 3 of the pinhole inspection apparatus, and the open end of the can body 1 is brought into contact with the open end receiving part 7. The rotating turret 5 is rotated gradually and positioned such that the through hole 8 in the rotating turret 5 is coaxial with the penetrating hole 21 in the movable plate 20, whereupon the rotating turret 5 is stopped to perform pinhole inspection.

To confirm the shielding effect of the shield mechanism, the air cylinder for pressing the movable plate 20 was not operated on purpose so that there was a gap of 0.12 mm (shim) between the movable plate 20 and the rotating turret 5. The shielding effect with and without the shield mechanism was ascertained based on the light detection values of the photodetector 13.

TABLE 1

| | Shim: 0.12 mm | |
| --- | --- | --- |
| Angle (°) | With shield mechanism (mV) | Without shield mechanism (mV) |
| −12 | 110 | 2020 |
| −6 | 290 | 2350 |
| 0 | 98 | 570 |
| 6 | 145 | 1100 |
| 12 | 139 | 940 |

As shown in Table 1, the light detection value measured when the angle was 0° was 98 mV when the shield mechanism was provided, while the light detection value was 570 mV when the shield mechanism was not provided.

The light detection values mentioned above are voltage values (mV) converted from the detected light amount.

From Test 1 and Test 2 described above, it is assumed that, when both shield mechanisms are provided, ambient light that was attenuated by the detour path in the shield mechanism formed by the pair of shield parts used in Test 1 to a reduced level is attenuated with an attenuation rate achieved by the shield mechanism of the movable plate used in Test 2.

Figure 9:
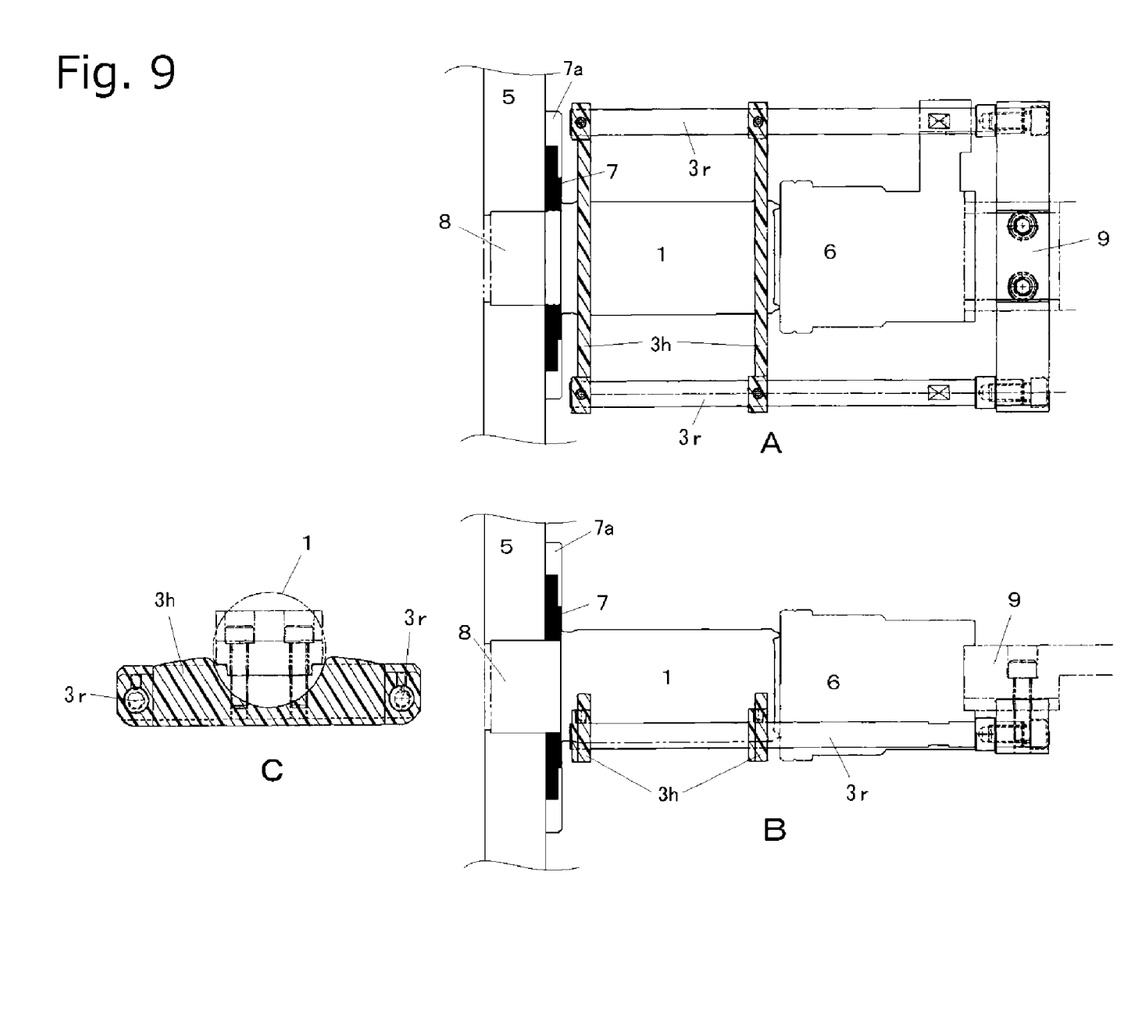
FIG. 9 is a diagram showing a mechanism for holding can bodies applicable to the present invention.

FIG. 9A to FIG. 9C illustrate can body holding members 3h that may be used instead of the previously described inspection turret 3 that holds the can body. FIG. 9A is a bottom view, FIG. 9B is a front view, and FIG. 9C is a side view of the can body holding members 3h holding a can body 1.

The can body holding members 3h are plate-like members having a recess in an upper part in which the can body 1 can be placed. They are secured to a support shaft 9 of a chuck 6 that supports the bottom of the can body via rods 3r. The can body holding members 3h are attached on a plurality of rods 3r with a predetermined distance therebetween so as to hold near upper end and lower end of the body part of the can body 1. The can body holding members 3h and the chuck 6 are movable along an axial direction relative to the rotating turret 5 to bring the open end of the can body 1 into tight contact with the open end receiving part 7 of the rotating turret 5 by means of a cam and a cam follower (not shown).

With this configuration, the inspection turret 3 is made unnecessary, so that the degree of freedom for installing the light source 10 (in particular, lower light source 10b) for irradiating the can body 1 with light is increased, and it is possible to provide more light sources to increase the light amount. Also, defects such as scars or dents in the body part of the can body 1, which may result from sliding with a can body placement portion in the pocket 3a of the inspection turret 3 as the can body 1 moves axially relative to the rotating turret 5, can be prevented.

According to the pinhole inspection apparatus for can bodies of the present invention, by providing a detour path formed by a pair of shield parts as a shield mechanism, ambient light can be attenuated or shielded as it propagates through the complex detour path, so that entrance of ambient light to a photodetector side through a gap between a movable plate and a rotating turret that may be formed due to a surface condition or the like can be effectively prevented.

In the pinhole inspection apparatus for can bodies of the present invention, by providing a shield mechanism additionally to the movable plate, the effect of attenuating or shielding ambient light can be increased further.

The increased light shielding effect enables the pinhole inspection apparatus for can bodies of the present invention to use a high brightness light source and to detect pinholes with an even smaller diameter (of about several μm), and thus a pinhole inspection apparatus for can bodies with improved inspection precision can be provided.

The invention claimed is:

1. A pinhole inspection apparatus for can bodies, comprising:
    a rotating turret having a penetrating through hole;
    a movable plate provided on a stationary frame opposite the rotating turret;
    a can body holding member supporting a body part of a can body;
    a photodetector detecting light leaking inside the can body; and
    a light source irradiating an outer circumferential surface of the can body with light, wherein
    a detour path formed by a pair of shield parts spaced apart a predetermined distance and opposite from each other is provided as a shield mechanism in an entire outer peripheral region of the rotating turret.

2. The pinhole inspection apparatus for can bodies according to claim 1, wherein the pair of shield parts include a first shield part and a second shield part, the first shield part being fixedly attached to the rotating turret, and the second shield part being fixedly attached to a position substantially opposite a side face part of the rotating turret.

3. The pinhole inspection apparatus for can bodies according to claim 1, wherein the pair of shield parts include a first shield part and a second shield part, and shield members provided to the respective shield parts protrude alternately toward tubular parts of the respective shield parts opposite each other.

4. The pinhole inspection apparatus for can bodies according to claim 2, wherein the pair of shield parts include a first shield part and a second shield part, and shield members provided to the respective shield parts protrude alternately toward tubular parts of the respective shield parts opposite each other.

5. The pinhole inspection apparatus for can bodies according to claim 3, wherein the shield members are shield plates protruding orthogonally to the tubular parts of the respective shield parts opposite each other.

6. The pinhole inspection apparatus for can bodies according to claim 3, wherein the shield member faces another shield member with a distance of 5 mm or less.

7. The pinhole inspection apparatus for can bodies according to claim 6, wherein the shield member overlaps another shield member opposite thereto over a length of 9 mm or more.

8. The pinhole inspection apparatus for can bodies according to claim 1, wherein a plurality of annular grooves having a rectangular cross section and concentric to a penetrating hole of the movable plate are formed in a surface of the movable part as a shield mechanism.

9. The pinhole inspection apparatus for can bodies according to claim 1, wherein the light source is a white LED light source.

10. The pinhole inspection apparatus for can bodies according to claim 8, wherein the light source is a white LED light source.

11. The pinhole inspection apparatus for can bodies according to claim 1, wherein the can body holding member is secured to a support shaft of a chuck via a rod.

12. The pinhole inspection apparatus for can bodies according to claim 8, wherein the can body holding member is secured to a support shaft of a chuck via a rod.

* * * * *